United States Patent
Koumans

(10) Patent No.: US 11,946,016 B2
(45) Date of Patent: Apr. 2, 2024

(54) PROCESS FOR THE EXTRACTION OF OIL-SOLUBLE COMPONENTS FROM PLANT MATERIAL

(71) Applicant: BioSoma B.V., Delft (NL)

(72) Inventor: Floris Jan Robert Koumans, Delfgauw (NL)

(73) Assignee: BioSoma B.V., Delft (NL)

( * ) Notice: Subject to any disclaimer, the term of this patent is extended or adjusted under 35 U.S.C. 154(b) by 0 days.

(21) Appl. No.: 17/252,250

(22) PCT Filed: Jun. 14, 2019

(86) PCT No.: PCT/NL2019/050365
§ 371 (c)(1),
(2) Date: Dec. 14, 2020

(87) PCT Pub. No.: WO2019/240581
PCT Pub. Date: Dec. 19, 2019

(65) Prior Publication Data
US 2021/0189287 A1    Jun. 24, 2021

(30) Foreign Application Priority Data

Jun. 14, 2018  (EP) ................................... 18177817
Mar. 20, 2019  (EP) ................................... 19164090

(51) Int. Cl.
*C11B 1/10*  (2006.01)
*A61K 36/185*  (2006.01)

(52) U.S. Cl.
CPC ............ *C11B 1/102* (2013.01); *A61K 36/185* (2013.01); *C11B 1/10* (2013.01); *C11B 1/108* (2013.01);
(Continued)

(58) Field of Classification Search
CPC . C11B 1/10; C11B 1/108; C11B 1/102; C07B 63/00; C07D 311/80
See application file for complete search history.

(56) References Cited

U.S. PATENT DOCUMENTS 9,587,203 B2 *  3/2017  Wasserman ............ B01D 11/02
9,732,009 B2 *  8/2017  Raber ..................... A61P 25/04
(Continued)

FOREIGN PATENT DOCUMENTS

WO        2016/064987 A1    4/2016
WO    WO 2018/006165 A1 *  1/2018 ........... A61K 36/185
(Continued)

OTHER PUBLICATIONS

Dayanandan, P. et al., Trichomes of cannabis sativa L. (Cannabaceae)., Journal of Botany, 63(5), pp. 578-591 (Year: 1976).*
(Continued)

*Primary Examiner* — Yate' K Cutliff
(74) *Attorney, Agent, or Firm* — Studebaker & Brackett PC

(57) ABSTRACT

The invention is directed to a process for the extraction of one or more oil-soluble components from plant material, to an oil comprising one or more oil-soluble components from plant material, preferably obtainable by the process of the invention, a physiologically acceptable product comprising the oil, and to the use of plant material. The process of the invention comprises:
  a) providing oil and plant material;
  b) heating the oil to a temperature of 10-80° C., preferably 50-80° C.;
  c) contacting the oil with the plant material while the oil and plant material are in motion relative to each other, thereby extracting one or more oil-soluble components from said plant material;
(Continued)

d) replacing plant material with new plant material during the extraction process; and e) collecting said oil when the concentration of the one or more oil-soluble components has reached a desired level.

29 Claims, 5 Drawing Sheets

(52) U.S. Cl.
CPC .... *A61K 2236/331* (2013.01); *A61K 2236/39* (2013.01)

(56) References Cited

U.S. PATENT DOCUMENTS

| | | | | |
|---|---|---|---|---|
| 9,808,494 | B2* | 11/2017 | Barringer | A61K 36/185 |
| 9,950,275 | B1 | 4/2018 | Ruben et al. | |
| 2012/0095087 | A1* | 4/2012 | Hyatt | A61K 31/05 |
| | | | | 514/454 |
| 2017/0209809 | A1* | 7/2017 | Hopkins | B01D 11/0292 |
| 2017/0266153 | A1* | 9/2017 | Levy | A61K 33/00 |
| 2017/0312327 | A1 | 11/2017 | Jones | |

FOREIGN PATENT DOCUMENTS

| | | | | |
|---|---|---|---|---|
| WO | WO 2018/011808 | * | 1/2018 | ........... A61K 31/352 |
| WO | WO 2018/011808 A1 | * | 1/2018 | ........... A61K 31/352 |
| WO | 2018/023166 A1 | | 2/2018 | |
| WO | 2019/051560 A1 | | 3/2019 | |

OTHER PUBLICATIONS

Yar-Varon, E., et al., Vegetable oils as alternative solvents for green oleo-extraction, purification and formulation of food and natural products, Molecules, 22, 1474, pp. 1-24 (Year: 2017).*

Rooney; International Search Report and Written Opinion issued in PCT/NL2019/050365; dated Aug. 26, 2019; nine pages.

Anonymous; "Cannabis processing for THC, CBD & terpenes"; Sep. 18, 2014; eight pages; URL: http://landprofile.com/p/Salve.pdf [retrieved: Aug. 15, 2019].

Pavlovic et al.; "Quality traits of 'cannabidiol oils': Cannabinoids content, terpene fingerprint and oxidation stability of European commercially available preparations"; Molecules; May 20, 2018; 22 pages, vol. 23, issue 5, No. 1230.

Romano & Hazekamp; "Cannabis oil: Chemical evaluation of an upcoming cannabis-based medicine"; Cannabinoids; May 5, 2013; pp. 1-11; vol. 7, issue 1.

Phytoalchemy; "Extraction using lipid oils as a solvent"; Jan. 31, 2018; two pages; URL: https://www.reddit.com/r/CannabisExtracts/comments/7uac1n/extraction_using_lipid_oils_as_a_solvent/.

* cited by examiner

PROCESS FOR THE EXTRACTION OF OIL-SOLUBLE COMPONENTS FROM PLANT MATERIAL

BACKGROUND

Field of the Invention

The invention is directed to a process for the extraction of one or more oil-soluble components from plant material, to an oil comprising one or more oil-soluble components from plant material, to a physiologically acceptable product comprising the oil, and to the use of the plant material.

The invention relates to the extraction and refining of oil-soluble substances from biological material. Oils derived from plant matter are desirable in a wide variety of industries and applications.

Description of Related Art

*Cannabis* is well-known for the active ingredients contained therein and on the plant material itself. The active ingredients in *Cannabis* species, including *Cannabis* indica and *Cannabis sativa*, have been found to have properties beneficial to health. Medicinal properties are attributed to *Cannabis* as well, including relief of symptoms of various diseases and conditions.

Commonly known *Cannabis* derived products are hemp and marijuana. Both hemp and marijuana are of the same genus, *Cannabis*, and the same species, *Cannabis sativa*. However, which term applies depends on how the plant is grown and utilised. Typically, the term *cannabis* (or marijuana) is used when describing a *Cannabis sativa* cultivar having high amounts of $\Delta^9$-tetrahydrocannabinol (THC), the cannabinoid most known for its psychoactive properties. Hemp (or industrial hemp), on the other hand, is used to describe a *Cannabis sativa* cultivar that contains only trace amounts of THC. Hemp is a high-growing plant, typically cultivated for industrial uses such as oils and topical ointments, as well as food for humans and animals (e.g. seeds) and also fibre for clothing, construction, etc. The term "hemp" as used herein is meant to refer to a *Cannabis sativa* cultivar that contains less than 0.3% by total weight of the plant of THC, in particular less than 0.2%.

*Cannabis* contains a relatively unique class of compounds, the cannabinoids. Cannabinoids are compounds with 21 carbon atoms and carboxylic acids, analogues and transformation products of the 21-carbon compounds (the carboxylic acids are particularly prevalent in living cells and fresh plant product until aging, drying and/or heat decarboxylate them). There are well over a hundred different cannabinoids produced in epidermal trichomes, but few are present in appreciable quantities, and relatively few have adequate pharmacological data available. Trichomes are epidermal appendages present on aerial parts in most plant species and these trichomes have many proposed functions. Usually they are considered a protection against predators and pests. There are several classes of epidermal secretory glandular trichomes in *Cannabis*, all of which produce cannabinoids. Most tetrahydrocannabinol (THC) is located in the resin heads of capitate-stalked glandular trichomes. The highest concentration of cannabinoid resin is found in trichomes on the perigonal bracts which envelop the pistils and seeds. Glandular trichomes are also concentrated on the lower surface of young leaves, and on sepals and anthers. The primary cannabinoids produced in glandular trichomes are cannabigerol (CBG), cannabichromene (CBC), cannabidiol (CBD), $\Delta^9$-tetrahydrocannabinol (THC), and cannabinol (CBN). Their relative percentage in *Cannabis* varies greatly with genetic and environmental factors. The non-intoxicant CBG is the precursor of the other cannabinoids. CBC is a non-intoxicant type found in trace amounts. There is generally an inverse relationship between THC and CBD in *Cannabis*. Marijuana species can produce THC in high levels, while industrial hemp cultivars produce primarily CBD.

One of the products that can be made from industrial hemp is CBD oil. CBD oils and tinctures are usually made with hemp extracts, which are often claimed to contain all of the beneficial cannabinoids and elements of the hemp plant, not just isolated CBD, but also a variety of minor components (in particular terpenes) which together give rise to a so-called "entourage effect". Contemporary extraction processes, however, do not discriminate between desirable and less desirable isolates, let alone preventing concentration loss of beneficial compounds. In the general market almost all CBD products are all diluted with oil, such as olive oil and/or hemp seed oil.

Getting the active components from the plant tops, having the highest trichome concentration, is crucial in processing and extraction of the active components of the *Cannabis* plant.

Most of the known extraction methods are based on carbon dioxide extraction and alcohol extraction.

For example, US-A-2004/0 049 059 describes a method for producing an extract from *Cannabis* plant matter, containing tetrahydrocannabinol, cannabidiol and optionally the carboxylic acids thereof, in which the dried plant matter is ground and subjected to extraction with supercritical carbon dioxide. The obtained primary extract is subsequently separated. This process requires dried plant material, is relatively expensive and rather complex. Moreover, the extracted material has to be transferred to an oily medium to obtain the final product. The described method further allows the loss of active (volatile) components during the process.

US-A-2003/0 017 216, on the other hand, describes a method for preparing a *Cannabis* extract comprising contacting *Cannabis* plant material with a solvent for an amount of time less than that necessary for the solvent to reach an equilibrium concentration of cannabinoids, and separating the solvent and dissolved cannabinoids from the *Cannabis* plant material. The preferred solvent, also used in the examples, is denatured ethanol. Also in this process, the extracted material has to be transferred to an oily medium. Such transfer is an additional process step which can be accompanied with loss of valuable components. Furthermore, ethanol extraction is subjected to regulatory provisions and has several potential hazards associated therewith, e.g. flammable hazard.

WO-A-2016/064987 describes an extract comprising cannabinoids and at least one terpene/flavonoid. The extract may be obtained from *Cannabis* plant material by hydrocarbon extraction, supercritical $CO_2$ or NEOBEE 896 MCT, and is subsequently winterised by any method known in the art, for example by adding cold ethanol, thereby producing a waxy precipitate.

US-A-2017/0 209 809 describes an organic oil extraction device and method for performing butane hash oil extraction. The extraction is performed with (volatile) butane.

US-A-2016/0 213 720 describes the extraction of cannabinoids from *Cannabis* using lipids as an extraction solvent. The process is exemplified by means of an apparatus having two vertical extraction chambers (columns) holding plant material through which lipid solvent is circulated until the extraction is complete. This process only allows to achieve a limited concentration of active ingredients up to the point where the plant materials contained in the extraction chambers is exhausted. Further concentration requires additional processing steps or emptying and refilling the extraction chambers, which is time-consuming and costly.

There remains a need in the art for further and improved processes to extract oil-soluble components from plant material.

SUMMARY

Objective of the invention is to address one or more of the disadvantages faced in the prior art.

A further objective of the invention is to provide a simple, low-cost process for extraction of oil-soluble components from plant material.

Yet a further objective of the invention is to provide an oil comprising a relatively high terpene to cannabinoids ratio.

Yet a further objective of the invention is to extract oil-soluble components from plant material while minimising loss of (volatile) active components.

Yet a further objective of the invention is to provide a convenient process for extracting oil-soluble components from intact fresh plant material.

Yet a further objective of the invention is to allow the increase of the concentration of active oil-soluble components in the end-product.

Yet a further objective of the invention is to enable a variation in specific active oil-soluble components in the end-product.

Yet a further objective of the invention is to allow the addition of other beneficial oil-soluble components which are foreign to the plant material, in order to obtain specific added value in the end-product.

It was found that one or more of these objectives can be met, at least in part, by providing a process wherein oil is in dynamic contact with plant material, i.e. oil and plant material are in motion relative to each other, and wherein plant material is replaced with new plant material during the extraction process.

Accordingly, in one aspect the invention is directed to a process for the extraction of one or more oil-soluble components from plant material comprising:
  a) providing oil and plant material;
  b) heating the oil to a temperature of 10-80° C.;
  c) contacting the oil with the plant material while the oil and plant material are in motion relative to each other, thereby extracting one or more oil-soluble components from said plant material;
  d) replacing plant material with new plant material during the extraction process, and
  e) collecting said oil when the concentration of the one or more oil-soluble components has reached a desired level.

In a further aspect the invention is directed to an oil comprising one or more oil-soluble components from plant material, preferably obtainable by the process as described herein, wherein said oil comprises one or more cannabinoids and one or more terpenes, and wherein the total of cannabinoids and the total of terpenes are in a weight ratio of 200:1 to 5:1, such as 150:1 to 10:1, 100:1 to 20:1, or 50:1 to 25:1.

In a further aspect the invention is directed to a physiologically acceptable product comprising the oil as described herein.

In yet a further aspect the invention is directed to the use of the plant material collectable at step d) of the process as described herein in foodstuffs, e.g. animal feed and pet food, land spreading, anaerobic digestion, fabrics, and packaging.

DETAILED DESCRIPTION

Figure 1:
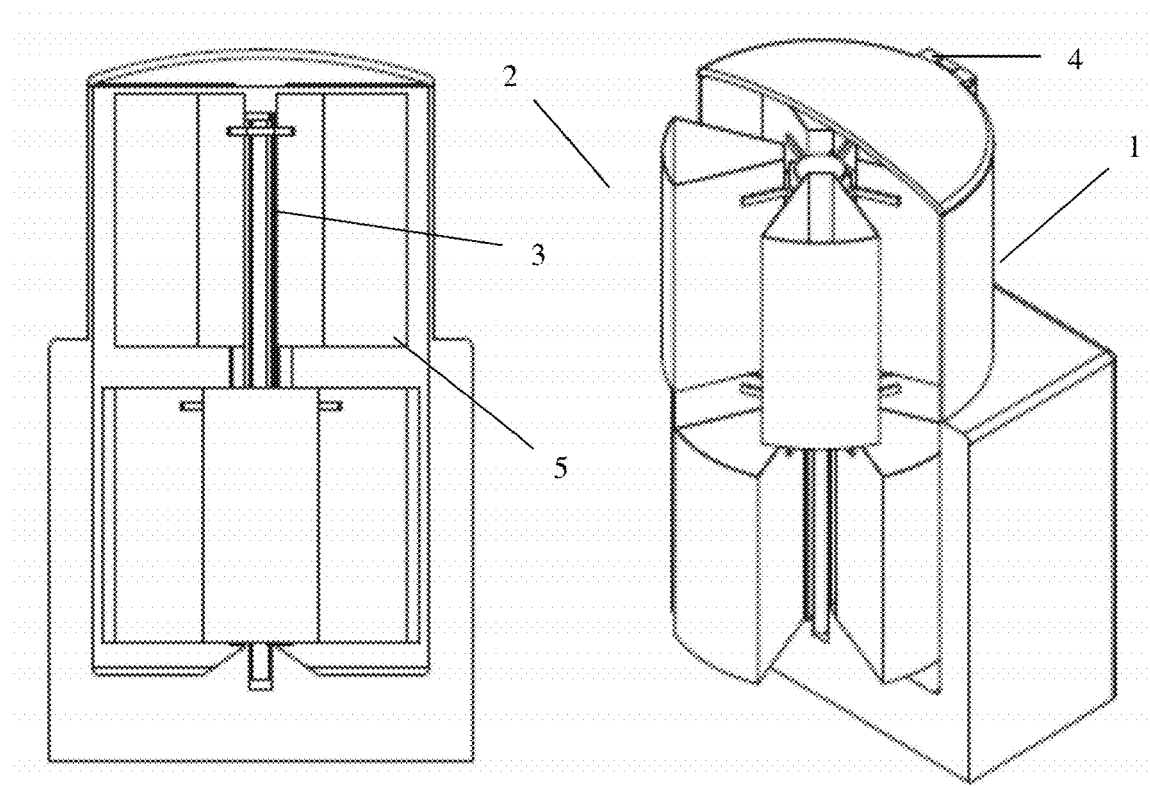
FIG. 1 shows a closable container.

The invention advantageously allows easy and effective extraction of oil-soluble components from plant material, preferably fresh plant material (i.e. plant material which has not been pre-treated, e.g. by drying). An additional advantage of the extraction process of the invention is its low cost, but at the same time allows to efficiently obtain an extract concentrated in oil-soluble components from the plant material. Advantageously, the invention allows the extraction of oil-soluble components from plant material at atmospheric pressure by means of a liquid extractant. The invention suitably allows the extraction of oil-soluble components from fresh plant material, such that the content of active components in the fresh plant material, including (volatile) terpenes, is affected only in a limited way. In general, pre-dried plant material has a lower active content (e.g. terpenes) than fresh plant material, hence fresh plant material is preferred with the invention. The use of pre-dried plant material may suitably require one or more additional pre-treatment and/or post-treatment steps of the plant material to minimise oil loss during the extraction process. Fresh plant material, may predominantly benefit from one or more additional post-treatment steps to minimise oil loss. Advantageously, the obtained concentrated extract is ready for use. For example, in case of a *Cannabis* extract, it may be used as CBD oil without further processing. It was further surprisingly found that the invention enables the extraction of high levels of oil-soluble components from plant material, such as terpenes and cannabinoids, in particular with fresh plant material. Particularly, a relatively high weight ratio of terpenes to cannabinoids can be achieved. The invention advantageously allows obtaining oil-soluble components from plant material comprising essentially no contaminants, such as chlorophyll, since the plant material is preferably intact.

The term "closable container" as used herein is meant to refer to an object for holding and/or transporting something, such as, for example a conduit, container, (closed) loop, vessel, kettle or bath. The closable container can, for instance, be made out of stainless steel and is preferably suitable for pharmaceutical, cosmetic and/or food processing. The container may preferably be closable by means of a removable or hinged cover for the top of the container, such as a lid, cover or covering. Preferably, the closable container forms a closable space for holding oil, plant material and/or reservoirs as described herein below. The closable container may comprise an inlet and/or outlet for charging, discharging and/or exchanging oil. In case an inlet and/or outlet is present, the closable container can be connected in series with one or more additional (closable) containers and/or be connected to, for example a closed loop, such as the closed loop as described herein.

The term "closed loop" as used herein, is meant to refer to a container in the form of a conduit configured so as to circulate oil, substantially without exchanging or discharging the oil outside of the conduit. The conduit itself can form an enclosed space holding the oil and which protects it from the environment, but it is also possible that the conduit forms a partially enclosed space holding the oil. Preferably, the closed loop forms an enclosed space holding the oil. Exposure to air may, for example, result when opening the closable container in order to replace the plant material with (new) plant material. Consequently, the term "closed loop" as used herein is meant to include "semi-closed loop" since the closed loop can be opened and closed. In fact, the closed loop is a closable loop.

The term "dynamic flow" as used herein is meant to include the motion of oil and plant material relative to each other.

The term "extracting" as used herein is meant to refer to separating one or more oil-soluble components from plant material and/or dissolving one or more oil-soluble components from plant material. The process of the invention is suitable for extracting oil-soluble components from the surface of the plant material.

The term "intact" as used herein is meant to include plant material which has not been pre-treated in the sense of milling, crushing, grinding, cutting, mashing, etc. The use of intact (fresh) plant material has the advantage of avoiding the extraction of significant levels of contaminants from the plant material, i.e., predominantly by avoiding damaging plant tissue (cell structures) in such a way that contaminants (e.g., chlorophyll) are released, and further minimises the loss of active ingredients from the plant material since additional process steps are not required for the extraction of one or more oil-soluble components from the plant material.

The process of the invention is based on the extraction of one or more oil-soluble components from plant material by means of contacting oil with plant material while the oil and plant material are in motion relative to each other. In particular, the one or more oil-soluble components may be present on the surface and/or just below the surface of the plant material. In accordance with the process, the oil used for the extraction process is heated, since an oil temperature of 10-80° C. promotes the extraction of oil-soluble components when in contact with plant material. The relative motion of plant material and oil contributes to increased extraction efficacy in that the dissolution of oil-soluble components from plant material is enhanced. The replacing of plant material with new plant material during the extraction process may be performed intermittently or without needing to interrupt and/or stop (shutdown) the extraction process, resulting in a semi-continuous or continuous extraction process.

The process of the invention may further comprise one or more pre-treatment steps of the plant material, for example to minimise oil loss or to optimise the extraction of oil-soluble components. In the case of plant material comprising trichomes, pre-treating the plant material may also improve the accessibility of the trichomes. In particular, one or more pre-treatment steps may be performed when handling pre-dried plant material. Exemplary pre-treatment steps include soaking of plant material (e.g., in an aqueous medium, such as water), thereby lowering the amount of oil that can be absorbed by the plant material, in particular dried plant material, and crushing, milling and/or grinding of plant material. In case such a step or steps are performed, these preferably precede step a) of the process as described herein.

The process of the invention may further comprise one or more post-treatment steps of the plant material, for example to minimise oil loss, optionally alongside one or more pre-treatment steps. In particular, one or more post-treatment steps may be performed when handling predried plant material. The one or more post-treatments steps may be performed during step d), between steps d) and e), during step e), and/or after step e) of the process as described herein. Exemplary post-treatment steps include centrifuging plant material and pressing of plant material, thereby recovering absorbed and/or adsorbed said oil. Preferably, a post-treatment step of the replaced plant material at step d) is performed after step e) to minimise loss of one or more oil-soluble components.

By monitoring the concentration of the one or more oil-soluble components in the oil during the process, the concentration thereof in the end product can be controlled to a desired level. In addition, the monitoring can be performed either by having to interrupt the extraction process or without having to interrupt the motion of the oil and plant material relative to each other.

The invention further allows increasing the concentration of one or more (active) oil-soluble components in the end product by replacing plant material and adding new plant material during the extraction process. By using different types of plant material a variation in specific oil-soluble components in the end product can be achieved. The process of the invention further allows the addition of other beneficial oil-soluble components which are foreign to the plant material used during the extraction process.

The oil used in the process of the invention suitably comprises vegetable oil. Preferably, the oil comprises one or more selected from the group consisting of olive oil, grapeseed oil, safflower oil, canola oil, sunflower oil, coconut oil, hemp seed oil, palm oil, palm kernel oil, soybean oil, peanut oil, almond oil, cottonseed oil, and rapeseed oil. More preferably, the oil comprises olive oil and/or hemp seed oil. In particular, the oil used in the process may not require post-processing steps, such as filtration, separation, and purification. Furthermore, the oil used in the process preferably does not trigger physical allergic reactions.

The oil in the process of the invention is heated to a temperature of 10-80° C., preferably 25-75° C., such as 45-75° C., 50-70° C., or 55-65° C. This may, for example, be achieved using heating elements. The temperature is preferably maintained in this range during the extraction. One approach of maintaining the temperature approximately constant during the extraction can be by insulating at least part of the extraction process, to keep energy losses at a minimum. Such insulation is further advantageous to maintain congenial working conditions in proximity of the extraction process. At the above indicated temperatures, extraction of the oil-soluble components is promoted without (or while minimising) degradation of valuable components. In addition, by maintaining such temperatures (in particular 50° C. or more) for several hours, a slow pasteurisation process is realised by which microorganisms, e.g. pathogens, are eliminated. In particular, the oil may be heated to a temperature of at least 50° C. to efficiently extract one or more oil-soluble components from plant material according to the process as described herein. A temperature of the oil below 50° C. requires the extraction time to increase to elevate the content of extractants, hence resulting in a less efficient process. Heating to a temperature above 100° C. will damage the plant material by boiling at least part of its content. Suitably, the oil in the process according to the invention is heated to a temperature such that the extraction, or extraction and optional step of decarboxylation, as described herein, are positively affected, for example, 80° C. or more and/or 100° C. or less, such as 85-95° C.

In an embodiment, the process for the extraction as described herein is further performed with water and surfactant. The surfactant may be the (natural) emulsifier as described herein below. By using water with surfactant the oil-soluble components from the plant material, such as *Cannabis*, as described herein, are extracted. In addition, using water and surfactant (besides the oil), particularly results in isolating, e.g. trichomes from plant material. The composition of the extracted oil-soluble components does not change when an aqueous extractant is used.

In the process of the invention, plant material is brought into contact with the oil. Plant material can simply be added directly and/or indirectly to the oil, for example by means of a container, such as in one or more steeping reservoirs. Plant material can be removed from the oil by means of, for example a net, beaker, sieve, strainer, steeping reservoirs and/or tweezers. New plant material can be added directly to the oil, and/or by means of a container, such as a steeping reservoir.

In accordance with the invention, the oil and plant material are in motion relative to each other, preferably in continuous motion relative to each other. For example, the oil may be in continuous motion, or flow, relative to the plant material. In case the oil is in motion, such as flowing, it is advantageous that the oil flow does not have to be interrupted for replacement of plant material and/or for supplying additional material (as will be discussed below). The process allows for these process steps to be performed while the oil and plant material are in motion relative to each other, such as continuously flowing oil. Hence, the oil is preferably continuously flowing while replacing the plant material and/or while supplying additional material.

For example, the plant material may be contained in one or more steeping reservoirs. Preferably, these steeping reservoirs are flow-through reservoirs (such as baskets), so that the oil can easily flow through the reservoirs and contact the plant material. On the other hand, the steeping reservoirs should have a mesh size or pore (channel) distribution suitable to substantially prevent plant material from passing through the steeping reservoir into the oil. Accordingly, the steeping reservoir preferably has a mesh size of 10 mm or less, such as 8 mm or less, 6 mm or less, or 4 mm or less. The steeping reservoir preferably has a mesh size of 0.5 mm or more, such as 1 mm or more, or 2 mm or more. Nonetheless, it is not critical if some plant material passes through the mesh into the oil. Upon collecting the oil at the end of the process, the oil may be filtered to get rid of such undesired material.

The replacing of plant material with new plant material (i.e. plant material that has not previously been used for extraction) can, for example be performed by removing one or more steeping reservoirs holding plant material from the oil (flow) and placing one or more steeping reservoirs holding new plant material into the oil (flow). Plant material that is in contact with the oil may at least in part or entirely be replaced with new plant material. One of the advantages of the process as described herein is that the plant material does not necessarily need to be replaced entirely with new plant material during extraction nor does the motion of the oil relative to the plant material be interrupted when replacing plant material with new plant material. Preferably, plant material is semi-continuously replaced with new plant material during extraction. This is preferably done without significantly affecting the extraction process of the one or more oil-soluble components from the plant material, e.g. (significant) concentration loss of the one or more oil-soluble components, such as through volatilisation and/or oxidative degradation. The amount of new plant material, that replaces the plant material (i.e. preferably the plant material that is exposed to the extraction) may be less than, equal to, or more than the amount of plant material it replaces. For example, the amount of plant material replaced with new plant material may be, for example fives times less, four times less, three times less or two times less, the same amount, or, for example two times as much, three times as much, four times as much or five times as much as the plant material that is still in contact with the oil.

It is preferred to stepwise replace parts of the plant material that is in contact with the oil with fresh plant material, e.g. in two or more steps, such as 2-30 steps, 3-20, steps or 4-10 steps. In each individual replacement step, for example, 10% or more by total weight of plant material that is in contact with the oil may be replaced, such as 20% or more, 30% or more, 40% or more, or 50% or more. During that same replacement step, another part of the plant material is not replaced and remains in contact with the oil, for example, 90% or less by total weight of the plant material that is in contact with the oil, such as 80% or less, 70% or less, 60% or less, or 50% or less. Preferably, plant material in contact with the oil is consecutively replaced, such that in each replacement step, plant material which has been in contact with the oil for the longest time is replaced.

The plant material as described herein has a moisture content of 1-95% by total weight of the plant material. Fresh plant material as described herein is particularly meant to include plant material having a moisture content (or water content) of 50-95% by total weight of the plant material. Preferably, the moisture content of the fresh plant material is 60% or more compared to the initial moisture content of the fresh plant material (i.e. the moisture content of harvested plant material), such as 75% or more, 85% or more, or 90% or more. Alternatively, the plant material may have a moisture content of 1-30% by total weight of the plant material, and is consequently coined as dry plant material (including dried plant material, and pre-dried plant material). Preferably, the moisture content of the dry plant material is 20% or less compared to the initial moisture content of the fresh plant material (i.e. the moisture content of harvested plant material), such as 15% or less, 10% or less, or 5% or less. An advantage of dry plant material is its improved shelf life and lower total weight compared to fresh plant material.

By replacing the plant material with new plant material every once in a while, the concentration of oil-soluble components in the oil can be increased. Typically, the plant material is replaced when 30% or more, 45% or more, 50% or more, or 65% or more by total weight of the trichome material is dissolved, preferably 80% or more. Depending on the exact conditions and dimensions, this translates to an extraction time of 0.5-3 hours in the oil, such as 1-2 hours. In particular, the extraction time in the oil is 90 minutes or less, and 10 minutes or more, 15 minutes or more, 20 minutes or more, 30 minutes or more, 50 minutes or more, or 75 minutes or more. Preferably, the extraction time is 15-90 minutes, such as 25-80 minutes, 35-70 minutes, or 40-60 minutes. Hence, the concentration of oil-soluble components in the oil can be built up to a desired level by replacing plant material for new plant material multiple times.

In the case reservoirs are used, it is preferred to use two or more steeping reservoirs, such as 2-20 steeping reservoirs, 4-16 steeping reservoirs, or 6-12 steeping reservoirs. Preferably, the process comprises multiple steeping reservoirs holding plant material which are replaced non-simultaneously, such as alternately. This has the advantage that the oil is constantly in contact with plant material.

Preferably, when using reservoirs, replacing the plant material may involve lifting one or more steeping reservoirs containing plant material above the oil surface and allowing the plant material to drain for a period of time in order to minimise the loss of oil while replacing the plant material. In particular, the plant material may be allowed to drain for a period of time of 10 seconds or more, such as 30 seconds or more, 1 minute or more, or 5 minutes or more. The plant material may be allowed to drain for a period of time of 30 minutes or less, such as 20 minutes or less, 15 minutes or less, or 10 minutes or less. In the case of dry plant material, the time to drain is preferably at least 15 minutes. Suitably, the steeping reservoir may be locked into a position above the oil level so that the plant material can be drained. After the drain period, the plant material can be replaced with new plant material, or the steeping reservoir containing the plant material can be replaced with a steeping reservoir containing new plant material. Alternatively, a steeping reservoir containing new plant material may be placed in the oil while draining the plant material contained in another steeping reservoir above the oil level. In addition, the steeping reservoir above the oil level may even be removed when replacing the steeping reservoir containing the new plant material. Optionally, the one or more steeping reservoirs containing plant material are additionally agitated in order to enhance the release and/or extraction of oil-soluble components. This may, for instance, comprise one or more techniques selected from turning, shaking and vibrating. In particular, vibrating can include ultrasonic vibrations.

The invention is particularly directed to plant material that comprises trichomes. Preferably, the plant material comprises *Cannabis* plant material, such as *Cannabis sativa* plant material. More preferably, the plant material comprises industrial hemp and/or marihuana. In particular, the plant material comprises trichomes from industrial hemp. Trichome material (including cannabinoids and active oil-soluble components) will dissolve into the oil, while remaining plant material will, for example remain in the steeping reservoirs (when used).

The one or more oil-soluble components that are extracted in the process of the invention suitably comprise one or more selected from the group consisting of cannabinoids, flavonoids, and terpenes. Preferably, the one or more oil-soluble components comprise one or more selected from the group consisting of cannabigerol, cannabichromene, cannabidiol, $\Delta^9$-tetrahydrocannabinol, and cannabinol. The quality of the extracted one or more oil-soluble components can be determined by High Performance Liquid Chromatography (HPLC, also known as High Pressure Liquid Chromatography), Gas Chromatography (GC), and/or Inductively Coupled Plasma (ICP). HPLC is preferably deployed for the analysis of cannabinoids, whereas terpenes are preferably analysed by GC.

It is surprisingly found that (mechanically) pre-treating plant material, for example, by means of shredding and/or grinding, tends to result in elevated concentrations of contaminants, such as chlorophyll. It is therefore preferred to use intact plant material with the process of the invention, in particular fresh intact plant material (i.e., plant material having a minimum of damage to the cell structures of the plant material).

The concentration of one or more of the oil-soluble components is optionally monitored during the extraction process. This may, for instance, involve the taking of samples and analysis thereof. For example, samples can be taken at regular intervals and analysed. Analysis can be performed by any suitably analysis method known by the person skilled in the art. An example thereof is High Performance Liquid Chromatography (HPLC). This technique advantageously allows to assess the concentration of target oil-soluble components, such as cannabinoids, more preferably cannabidiol. When assessing the concentration of cannabinoids before decarboxylation, the analysis has to take into account that the molecular weight of the acidic cannabinoids will decrease with the molecular weight of carbon dioxide upon decarboxylation. Typically, in the process of the invention samples will be taken at regular intervals, depending on the volume of oil and amount of steeping reservoirs employed, and the concentration of one or more target oil-soluble components is determined. For small volumes, samples can be taken at intervals of 48 hours or less, 36 hours or less, 24 hours or less, 12 hours or less, 10 hours or less, 8 hours or less, 6 hours or less, 4 hours or less, 3 hours or less, 2 hours or less, 90 minutes or less, 60 minutes or less, 50 minutes or less, 45 minutes, 40 minutes, 35 minutes, 30 minutes or less, 25 minutes or less, 20 minutes or less, 15 minutes or less, or 10 minutes or less. Typically, the interval at which the concentration of the oil-soluble components is monitored will not be less than 5 minutes. Preferably, the concentration is monitored at intervals of 15 minutes or more.

If the monitoring shows that the concentration of target oil-soluble components is lower than the desired concentration level, then the process can be continued, possibly with additional new plant material. If the monitoring shows that the concentration of target oil-soluble components is higher than the desired concentration level, then additional oil may be added. If the monitoring shows that the concentration of target oil-soluble components is at the desired concentration level, then the process can be stopped and the oil can be collected (possibly after further optional steps, such as decarboxylation). The desired CBD concentration level is 50% or less. In particular, the concentration level can be 40% or less, 35% or less, 30% or less, 25% or less, 20% or less, 15% or less, 10% or less, or 5% or less. Preferably, the CBD concentration level is 1-30%, such as 2-25%).

The invention further allows adjusting the composition of the end product by correspondingly adapting the composition of plant material contained in the one or more steeping containers. This adjustment can be done during the process as a response to the outcome of the monitoring step. In this manner, specific weight ratios between different oil-soluble components can be tuned to a desired value. Examples of specific weight ratios between THC and CBD in the end product include, 22:1 or less, 14:1 or less, 8:1 or less, 6:1 or less, 2:1 or less, 1:1 or less, 1:4 or less, and 1:9 or less. It is also possible to prepare an oil end-product that is substantially free from THC. For example, wherein the THC concentration is 0.1% by total weight of the oil or less, such as 0.05% or less, or even 0.01% or less.

Optionally, the process of the invention comprises a step of decarboxylation. Decarboxylation is an important process for the activation of cannabinoids. In plant material these are typically present as acidic cannabinoids, but they can be converted to their neutral (active) form by decarboxylation. Decarboxylation may, for instance, comprise heating the oil wherein the one or more oil-soluble components are dissolved to a temperature of 80° C. or more, in the range of 80-100° C., preferably in the range of 85-90° C. Heating the oil below 80° C. does not have the desired effect of decarboxylation, whereas heating to a temperature of more than 100° C. may lead to a loss of volatile components, such as terpenes and/or flavonoids. This is undesirable, as such volatile components contribute to the "entourage effect". Heating to a temperature of more than 100° C. is possible and will speed up the process, but may result in an end product with lower quality, i.e. low amounts of terpenes and other volatile substances.

When heating the oil to a temperature in the range of 80-100° C., typically, the heating is performed for a period of 60-240 minutes, such as a period of 90-180 minutes. Preferably, the temperature is gradually heated, such as at a rate of 1-10° C./min, preferably 1-5° C./min. This helps in preventing possible loss of components such as cannabinoids, flavonoids, and terpenes.

Advantageously, the oil comprising one or more oil-soluble components does not need to be removed, but can be heated for decarboxylation of acidic cannabinoids. Preferably, the step of decarboxylation is performed when the desired concentration level of the one or more oil-soluble components has been reached, and before the oil is collected. Preferably, when heating the oil for decarboxylation, plant material and/or possibly present steeping reservoirs with plant material have been removed from the oil, such that oil is no longer in contact with plant material. During decarboxylation, there is thus preferably no plant material present in the oil, and preferably a free flow of oil. Depending in part on the temperature of the oil a certain degree of decarboxylation may occur during the extraction process. By flowing the oil a relatively homogeneous and gradual heating is achieved.

However, it is also possible to first collect the oil and in a subsequent step decarboxylate acidic cannabinoids in a separate container. When using such a separate container, it is preferred that the separate container is a closable container (that can be closed or left open), for example such as described herein below, so as to avoid (or minimise) the loss of volatile materials. Another possibility is to heat and/or dry the plant material before commencing the extraction process, in order to achieve decarboxylation of at least part of the acidic cannabinoids.

Preferably, the oil is filtered before being collected. This will allow the removal of any contaminations, such as pieces of plant material, foreign matter, and the like.

After collecting the oil, it may be optionally left to cool, and can then be used for further steps, such as packaging and encapsulation (e.g. in soft gel), or for use as an (active) ingredient in formulations, such as healthcare products.

Optionally, one or more additives may be added to the oil during the process of the invention. Depending on the additives, this may be done before or after the optional decarboxylation step. Typically, the one or more additives are oil-soluble. Some examples of suitable additives include one or more selected from vitamins, minerals, *cannabis* products, pharmaceutical ingredients, food ingredients, flavouring agents, emulsifiers, and the like. Since the oil is in motion relative to the plant material (dynamic oil flow), preferably continuously in motion, the dissolving of such additives into a homogeneous product is obtained during the process.

In a special embodiment, the process of the invention comprises a step of adding a natural emulsifier, such as lecithin or polyglycerol polyricinoleate. Such emulsifier allows to disperse the oil into many smaller fractions (as oil droplets) when used in the body and/or when in contact with water. In this manner the surface area can be considerably increased to improve the exposure of active oil-soluble components (such as cannabinoids) to the mucous membranes either of the oral cavity or the gastrointestinal tract. As a result, this may significantly increase the uptake of the active components (bio-availability) by the human body. Lecithin can be produced from any vegetable oil, including, but not limited to, soybean oil, sunflower oil, corn oil, cottonseed oil, palm oil and rapeseed oil. Preferably, the lecithin originates form soybean oil, because this source provides lecithin having relatively high amounts of phospholipids.

It may further be advantageous to add nitrogen or carbon dioxide to the extraction process to reduce the amount of oxygen. This may aid in preventing possible oxidation of components, and loss of (volatile) active components. The amount of oxygen directly above the oil can, for instance, be 5 vol. % or less, such as 3 vol. % or less by total volume of gas phase present above the oil.

In an embodiment, the oil is present in a closable container, and wherein said oil is in contact with plant material contained in one or more steeping reservoirs, thereby extracting one or more oil-soluble components from said plant material.

In an embodiment, the oil, such as the oil of step a) of the process of the invention, is continuously flowing in a closed loop, the oil is heated in said closed loop, and wherein said oil is contacted with plant material contained in one or more steeping reservoirs, thereby extracting one or more oil-soluble components from said plant material.

The oil which is continuously flowing in the closed loop can then be heated to a temperature of 10-80° C., preferably 25-75° C., such as 45-75° C., 50-70° C., or 55-65° C. The oil flow in this embodiment does not have to be interrupted for replacement of plant material and/or for supplying additional material. Hence, the oil is preferably continuously flowing while replacing the plant material and/or while supplying additional material.

The replacing of plant material with new plant material can be performed by removing one or more steeping reservoirs holding plant material from the oil flow in the closed loop and placing one or more steeping reservoirs holding new plant material into the oil flow in the closed loop.

Advantageously, the oil comprising one or more oil-soluble components does not need to be removed from the closed loop, but can be heated in the closed loop for decarboxylation of acidic cannabinoids.

Preferably, the oil is filtered before being collected from the closed loop. Suitably, one or more additives can be added directly into the closed tube.

The closed loop can be a closed tube, which is preferably filled (almost entirely) with oil. The tube is typically made out of stainless steel and is preferably an industrial piping suitable for pharmaceutical, cosmetic and/or food processing. The tube can have a diameter of 5 cm or more, such 10 cm or more, or 20 cm or more. The diameter is suitably 150 cm or less, such as 100 cm or less, or 80 cm or less.

The closed loop can suitably be provided with means for flowing the oil, for example one or more propellers and/or pumps. It is advantageous if these means allow to reverse the direction of the oil flow in the closed loop one or more times during the process. When the oil is flowing in a single direction for some time, plant material may accumulate at one side of the one or more steeping reservoirs. By reversing the oil flow direction one or more times during the process, such accumulated plant material will be shaken up or agitated. Thereby, the contact area of the plant material with the oil can be increased, and extraction of oil-soluble components from the plant material is enhanced. Accordingly, it is preferred that the direction of the oil flow in the closed loop is reversed (i.e. based on the direction of the oil flow relative to the plant material) one or more times during the process, such as two or more times, four or more times, or ten or more times.

Suitably, the closed loop will hold about 100-1000 litres of oil, preferably 200-900 litres, such as 300-800 litres, or 400-600 litres. Nonetheless, it is also possible to use smaller volumes for micro-production, such as volumes of 50-300 litres, 60-200 litres, or 70-150 litres. Higher volumes, such as 2000 litres or less, 3000 litres or less, 4000 litres or less, or even 5000 litres or less, are also possible and can be achieved by simply extending the length of the loop.

The closed loop may comprise one or more loops. This allows an engineering design to modularly expand the process, depending on the needs. By adding additional loops to the process, the total length of the closed loop system can be increased which not only allows for more steeping reservoirs to be placed into the oil flow thereby increasing capacity in plants, but also allows for increasing the output capacity by having more oil in the closed loop.

In practice, the closed loop (e.g. a closed tube) can, for example, be a tube having specific areas (e.g. chambers) in which steeping reservoirs (e.g. baskets) with plant material can be fitted in a practical manner so that they can easily be taken in and out of the loop. Typically, the closed loop will have multiple steeping reservoirs which are easy to handle. Preferably, the closed loop according to the invention is a horizontal loop. This advantageously allows to simply lower the steeping reservoirs lengthwise in the oil flow. For this purpose, the closed loop can be provided with one or more areas or chambers that is/are specifically designed for receiving the one or more steeping reservoirs. As an example, a tube can have one or more areas designed for placing baskets/reservoirs in the oil flow in a practical manner. The areas are preferably provided with a lid such that the loop can be closed once the steeping reservoir has been placed in the oil flow. The lid also allows opening the loop in order to replace a steeping reservoir holding plant material with a steeping reservoir holding new plant material. Preferably, the closed loop is on normal working height, such as at height of 50-120 cm above ground level, preferably, 60-100 cm above ground level. This has the advantage that users can readily access the closed loop and/or the steeping reservoirs with plant material contained therein. For users, it is further convenient if the weight of reservoirs including plant material is 30 kg or less, such as 25 kg or less, 20 kg or less, 15 kg or less, or 1-10 kg.

The oil in the closed loop is in continuous flow. The flow of oil may depend on the volume of the closed loop. Typically, the flow of the oil in the process can be, for instance, 0.01-20 l/min, such as 0.05-10 l/min, 0.1-5 l/min, 0.2-2.5 l/min, or 0.5-1.5 l/min.

The process of the invention is further based on relative motion between oil and plant material, preferably continuous motion. This may, for example, be a dynamic flow of oil, preferably continuous dynamic flow, in a closable container, such as a closed loop, which offers a variety of significant advantages over known processes for the extraction of cannabinoids.

In accordance with the process of the invention, plant material is brought in contact with oil, and preferably heated oil flows around in a closable container, such as a closed loop. One or more steeping reservoirs that contain plant material are placed in the oil flow. The flowing oil passes through the plant material in the steeping reservoirs. The oil contacts the plant material while in motion relative to each other. In this way, oil-soluble components can dissolve in the oil (are extracted from the plant material). The process thus involves dynamic oil extraction.

In view of the above, the process may be carried out in a closable container, such as a closed loop, which means that the oil is not exposed to air or at least that exposure to air (in particular oxygen) is minimised. This importantly allows to minimise the loss of volatile substances, as well as the possibility of oxidation, contamination and/or other possible factors that have an adverse impact on the quality of the extracted one or more oil-soluble components.

In a further embodiment (which may or may not be combined with the previous embodiments), the closable container is preferably semi-filled with the oil. The container is able to hold reservoirs, such as those described herein, which may at least in part be covered with the oil. In particular, the horizontal and/or vertical rotation or movement of at least one reservoir holding plant material inside the container results in a motion of the oil relative to the plant material. Plant material in a reservoir may be replaced with new plant material by vertically lifting the reservoir to above the oil level in the container. In case more than one reservoir is used, the dynamic flow is preferably not interrupted when replacing plant material with new plant material. In case of concurrently replacing all the plant material with new plant material, the dynamic flow may be interrupted.

Figure 2:
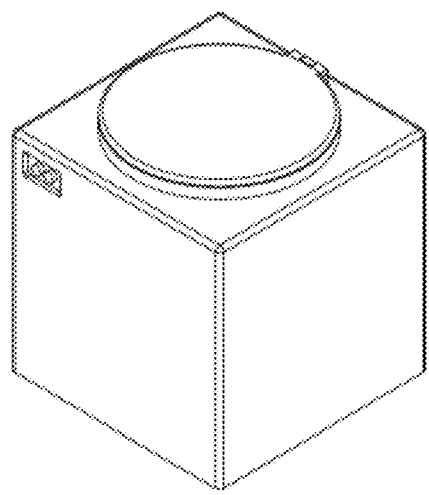
FIG. 2 shows a closable vessel wherein the vessel is retractable.

An example of a closable container as described herein is given by the schematic drawings in the FIGS. 1-4. FIG. 1 shows a closable container 1 having steeping reservoirs 2 which are connectable to a shaft 3 for holding the steeping reservoirs and/or agitate the medium held in the closable container. Closable container 1 further comprises a lid 4 to cover the vessel 5. Vessel 5 may be retractable, as can be seen in FIG. 2.

Figure 3:
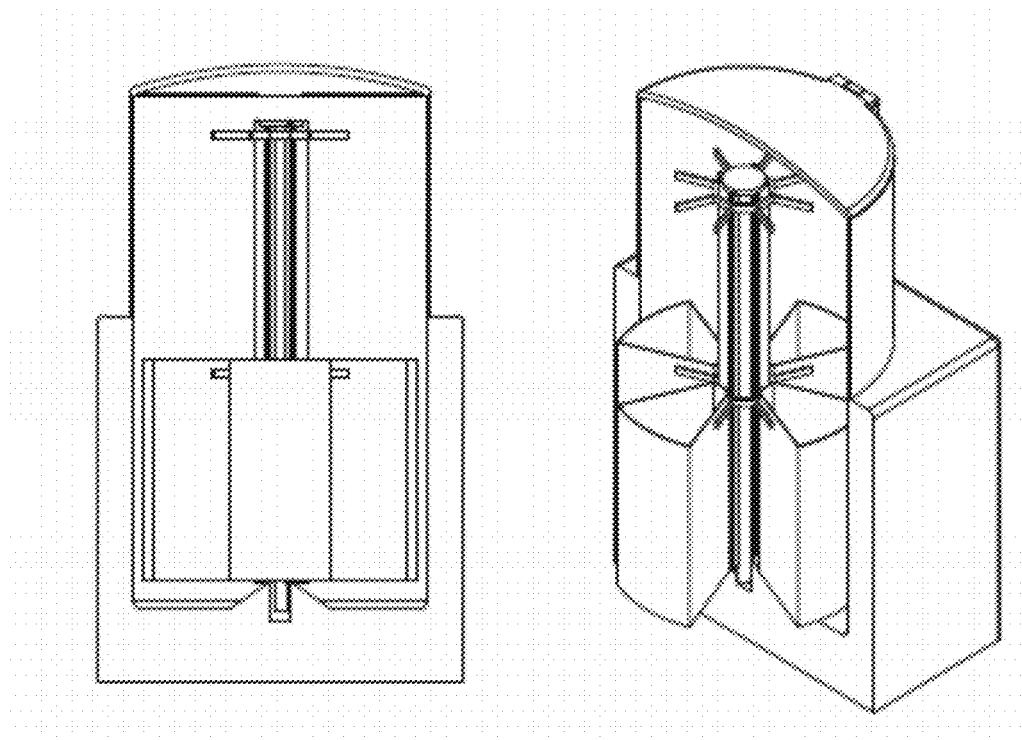
FIG. 3 shows a closable container wherein reservoirs are lowered.
Figure 4:
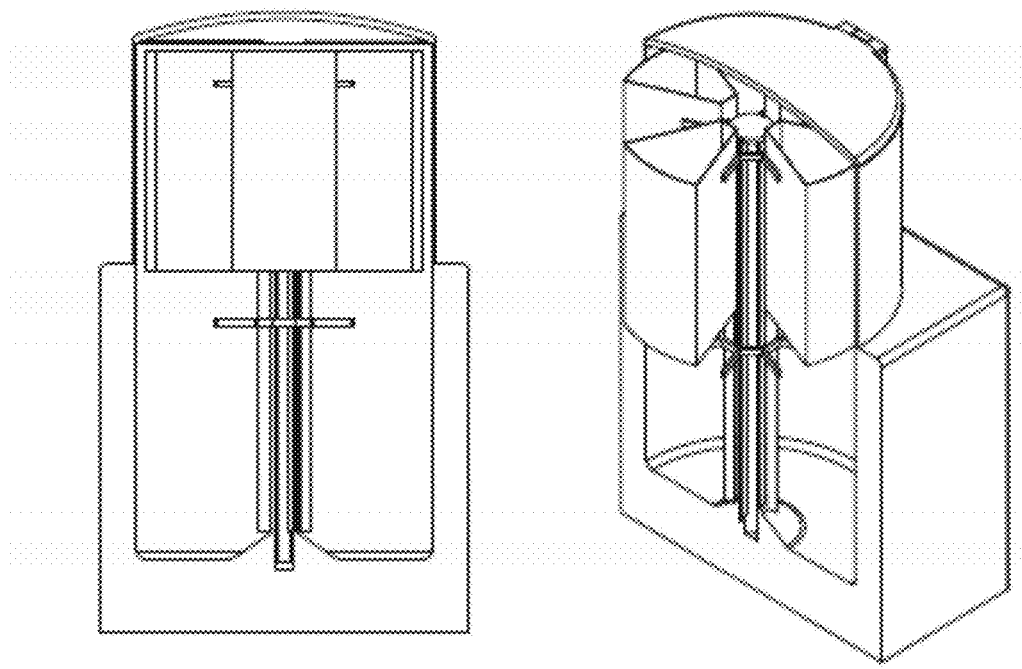
FIG. 4 shows a closable container wherein reservoirs are raised.

FIG. 3 shows the closable container wherein reservoirs are lowered, whereas FIG. 4 shows the closable container wherein the reservoirs are raised.

Figure 5:
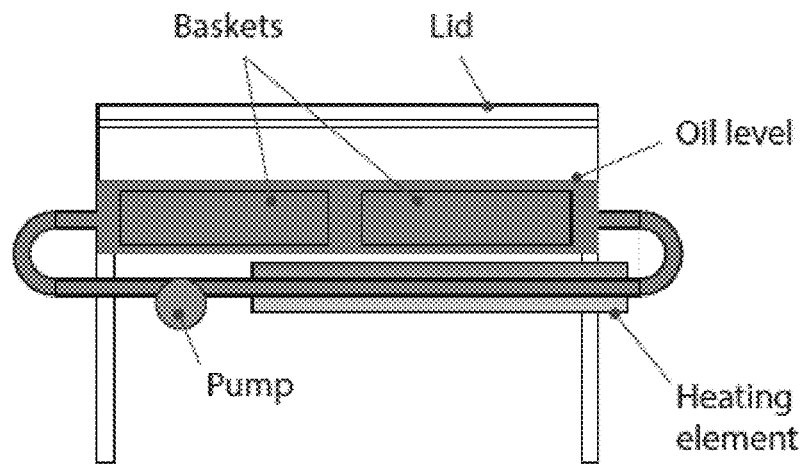
FIG. 5 shows a closable container wherein baskets are submerged in oil.
Figure 6:
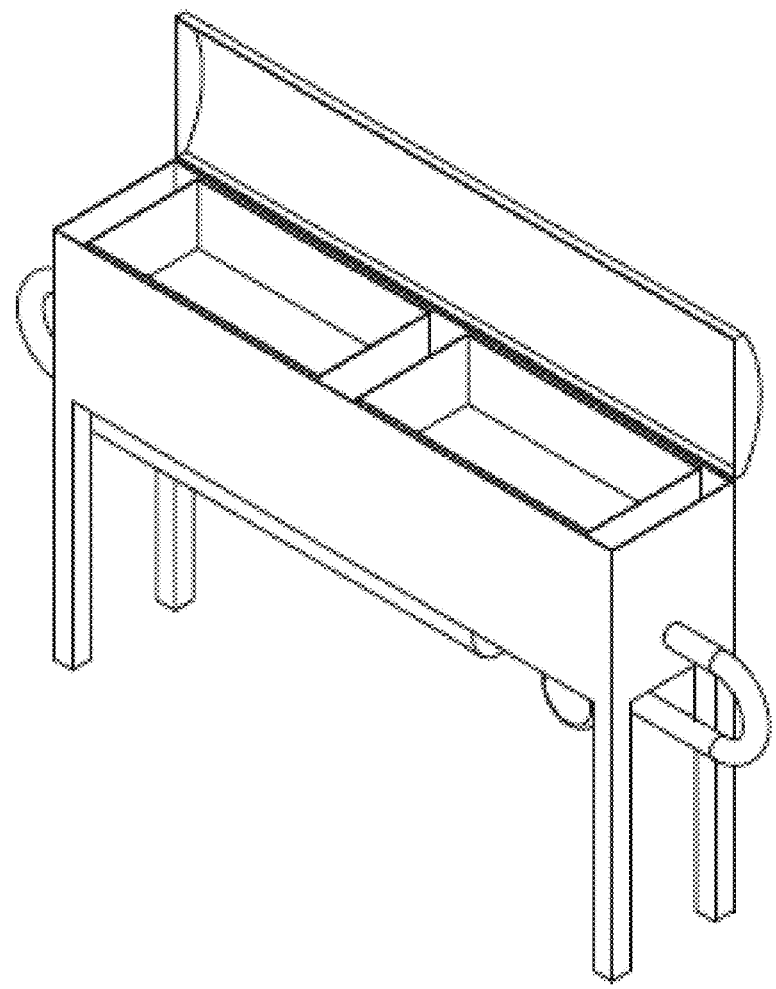
FIG. 6 shows a closable container wherein baskets are elevated above the oil level.

Another example of a closable container as described herein is given by the schematic drawings in the FIGS. 5 and 6. FIG. 5 shows the baskets submerged in oil, whereas FIG. 6 depicts the baskets elevated above the oil level.

In a further embodiment (which may or may not be combined with the previous embodiments), the closable container is able to hold reservoirs, such as those described herein, which are brought in motion relative to the oil that is present in the container. That is, the reservoirs are vertically and/or horizontally brought in motion in and/or out the container. Alternatively, the reservoirs are held in place while the oil is pumped through the container, thus achieving dynamic flow. Preferably, the dynamic flow remains uninterrupted when one or more of the reservoirs are lifted to above the oil level.

Contrary to prior art processes, the process of the invention allows to obtain an oil with oil-soluble plant extracts with a relatively high amount of volatile components. This is because the process of the invention, which can be performed in a closable container, such as a closed loop, and because the individual steps of the process, for example can all be performed within the same closable container (closed loop). Transfer steps (such as transfer into a different solvent) typically performed in prior art processes lead to a loss of volatiles. The process of the invention accordingly yields a unique oil that cannot be otherwise obtained.

Therefore, in a further aspect the invention is directed to an oil, comprising one or more oil-soluble components from plant material, that is preferably obtainable by a process according to the invention, wherein the oil comprises one or more cannabinoids and one or more terpenes, and wherein the total of cannabinoids and the total of terpenes are in a weight ratio of 200:1 to 5:1, such as 150:1 to 10:1, 100:1 to 20:1, or 50:1 to 25:1.

The oil of the invention preferably comprises one or more selected from the group consisting of cannabinoids, flavonoids, and terpenes. Preferably, the oil comprises one or more selected from the group consisting of cannabigerol, cannabichromene, cannabidiol, $\Delta^9$-tetrahydrocannabinol, and cannabinol. The oil of the invention can comprise 10% or less by total weight of the oil of CBD, such as 8% or less, 6% or less, 4% or less, or 2% or less. Preferably, the oil of the invention comprises about 5% by total weight of the oil of CBD. The oil of the invention can comprise THC. Preferably, the amount of THC in the oil of the invention depends on legislation and regulations.

The oil of the invention may comprise 0-15% of contaminants, such as chlorophyll, by total weight of the oil. In particular, the amount of contaminant(s), e.g. chlorophyll, may be 0.5-10 wt. %, such as 1-5 wt. %, or 1.5-2.5 wt. %. Preferably, essentially no chlorophyll is extracted and thus not present in the oil. The amount of chlorophyll present in the oil may indicate that the plant material with which the oil has been in contact was not intact, i.e. pretreated, such as by milling, grinding, crushing, etc.

In a special embodiment, the oil of the invention comprises a natural emulsifier, such as lecithin or polyglycerol polyricinoleate. The amount of emulsifier present in the oil may depend on the type and quality of the emulsifier used. For example, the amount of emulsifier in the oil may be 0.05-10% by total weight of the oil, such as 0.1-5%, or 0.1-4%, 0.2-3%, or 0.3-2%.

The oil can be directly physiologically used, i.e. for example applied to skin and/or intake (food/dietary supplement). In particular, the oil as described herein is suitable for physiological intake. A physiologically acceptable product comprising the oil and a (physiologically acceptable) carrier may suitably be used for physiological use. The carrier may be fluid, e.g. liquid, or solid. Suitable fluid carriers are, for example extracts (e.g. from plants), water, oils, such as an oil as those described herein, preferably a vegetable oil, or a mixture of water and oil. The oil may be a cannabidiol (CBD) oil in the case primarily Cannabis is used to obtain the oil. In case of the oil obtainable by the process as described herein, the oil used to extract the one or more oil-soluble components from the plant material suitably is the carrier. Suitable solid carriers are, for example non-nutrients and nutrients, such as nutritional organic compounds, proteins, amino acids, fatty acids, vitamins, salts and inorganic compounds, such as salts and minerals, e.g. mineral powder, coral powder, calcium carbonate, and (amorphous) silicon dioxide. In addition, suitable carriers may have a nutritional value, for example cacao-based products, such as chocolate.

The oil of the invention preferably comprises 0.1-5% by total weight of the oil of terpenes, and 1-25% by total weight of the oil of cannabinoids. The oil may comprise $\Delta^9$-tetrahydrocannabinol. In an embodiment, the oil is free of $\Delta^9$-tetrahydrocannabinol.

Cannabidiol may be present in the oil of the invention in an amount of 3-10% by total weight of the oil. In particular, the oil can comprise 3-9% by total weight of the oil of cannabidiol, such as 3.5-8%, 4-7%, or 4.5-6%, or 3-5%.

The oil of the invention comprises one or more terpenes. In particular, the terpenes in the oil may comprise terpenes commonly found in Cannabis. The oil comprises one or more terpenes, for example one or more selected from the group consisting of myrcene, pinene, such as $\alpha$-pinene and $\beta$-pinene, limonene, humulene, linalool, caryophyllene, ($\alpha$-)bisabolol, eucalyptol, nerolido, $\Delta^3$-carene, camphene, ocimene, guaiol, borneol, terpineol, valencene, geraniol and terpinolene.

The amount of terpene in the oil as described herein can be 0.01-5% by total weight of the oil, such as 0.02-4.5%, 0.03-4%, 0.04-3.5%, 0.05-3%, 0.1-2.5%, or 0.2-2%.

The oil may further comprise one or more flavonoids. In particular, the one or more flavonoids in the oil may comprise flavonoids commonly found in Cannabis. The flavonoids may, for example be selected from the group consisting of apigenin, cannaflavin A, cannaflavin B, cannaflavin C, isovitexin, kaempferol, luteolin, orientin, quercetin, silymarin, ($\beta$-)sitosterol and/or vitexin. The amount of flavonoids in the oil may be 0.1-10%, based on the total weight of the oil. In particular, the amount of flavonoids may be 0.25% or more, and 7.5% or less, 5% or less, or 2.5% or less by total weight of the oil. Preferably, the amount of flavonoids is 0.5-2 wt. %, such as 0.75-1.5 wt. %.

The invention also relates to a physiologically acceptable product comprising the oil as described herein, or the oil obtainable by the process as described herein, and further optionally comprising a carrier as described herein.

The physiologically acceptable product may be in a form suitable for oral application, such as in the form of a capsule, soft gel, tablet, pill, spray, vapour, drops, rinses, food, supplement, paste, powder, solution or pastille, or in a form suitable for topical application, such as in the form of a spray, vapour, drops, rinses, paste, solution, cream, foam, gel, lotion, ointment or tincture.

The invention also relates to a use of the plant material collectable at step d) of the process according to the invention in foodstuffs, e.g. animal feed and pet food, land spreading, anaerobic digestion, fabrics, and packaging.

The process of the invention can, for example, be performed with an extraction module for extracting oil-soluble components from plant material. The extraction module comprises a crop chamber having at least an inlet and an outlet, and a holding vessel characterised by having a structure through which fluid can flow, and for preventing plant material from passing through, wherein in use the holding vessel is situated inside the crop chamber. Preferably, the crop chamber of the extraction module has an opening on the topside that can be closed by means of a lid. The opening on the topside of the extraction module is suitable for placing and removing the holding vessel from the crop chamber. In addition, the inlet of the extraction module is preferably arranged oppositely to the outlet. The extraction module can be made from metal, wood, synthetic material, ceramic material, or a mixture thereof. In particular, the extraction module is capable of withstanding temperatures as mentioned above. Preferably, the holding vessel and interior of the crop chamber are made of a material or a material composite that is inert with respect to the extraction process according to the invention, i.e. material of the interior that does not dissolve, corrode or releases chemical components during the extraction process. Optionally, the holding vessel can be locked into position inside the crop chamber by means including handles connected to the holding vessel that rest in cavities present in the crop chamber.

The extraction module for extracting oil-soluble components from plant material can be used for the process of the invention by means of one extraction module, and at least two extraction modules as part of a continuous flow circuit. The extraction module is considered a modular extraction module when as part of the continuous flow circuit. The continuous flow circuit preferably comprises one or more pumps and/or propellers, and one or more extraction modules. The continuous flow circuit further optionally comprises at least one temperature regulation device with which allows controlling the temperature of the medium flowing through the continuous flow circuit.

In an embodiment, the continuous flow circuit comprises one extraction module and at least one pump and/or propeller. The continuous flow circuit further optionally comprises at least one temperature regulation device.

In a further embodiment, the continuous flow circuit comprises at least two extraction modules connected in series and at least one pump and/or propeller. The continuous flow circuit further optionally comprises at least one temperature regulation device.

In yet a further embodiment, the continuous flow circuit comprises at least two extraction modules connected in parallel and at least one pump and/or propeller. The continuous flow circuit further optionally comprises at least one temperature regulation device.

Figure 7:
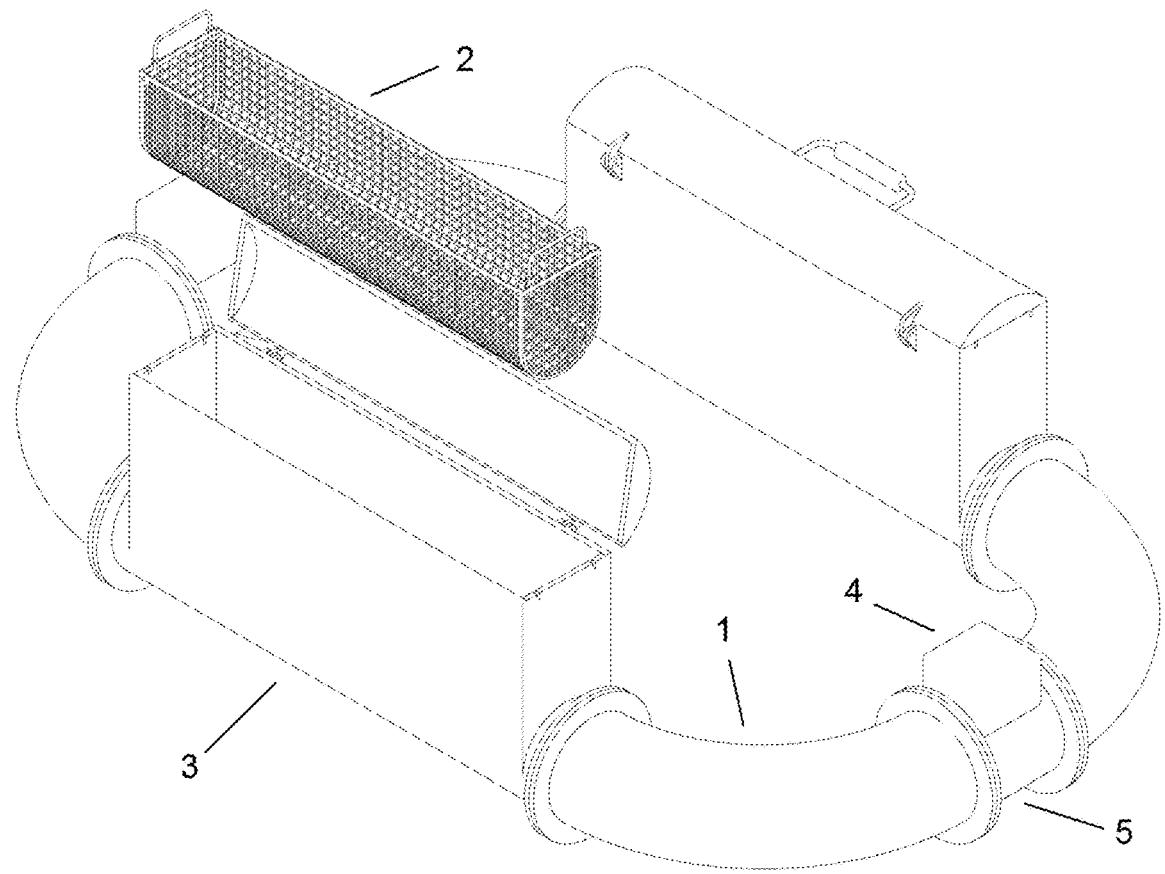
FIG. 7 shows a closed loop.
Figure 8:
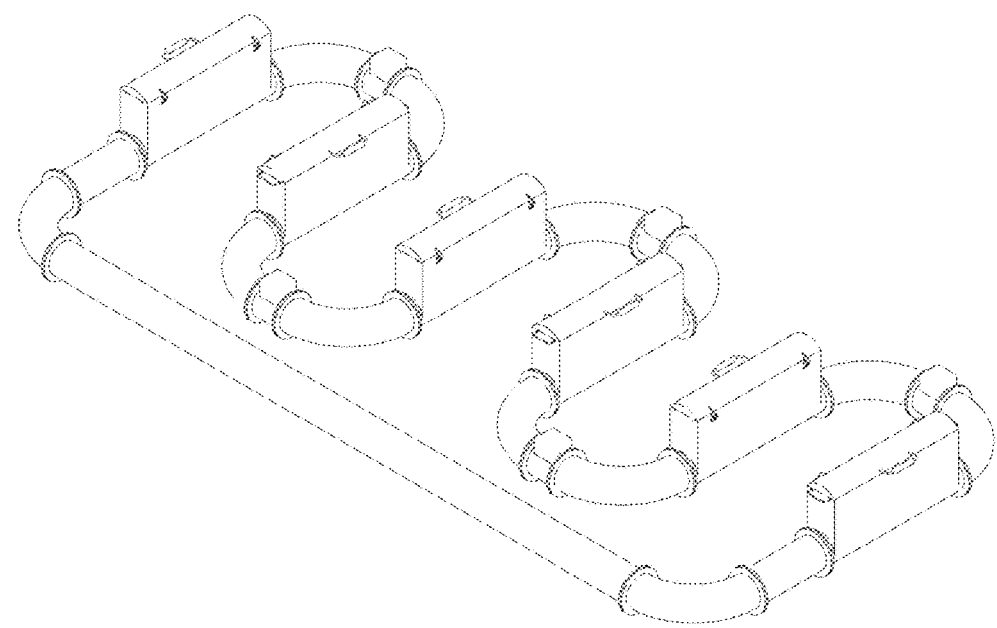
FIG. 8 shows a closed loop comprising multiple loops.
Figure 9:
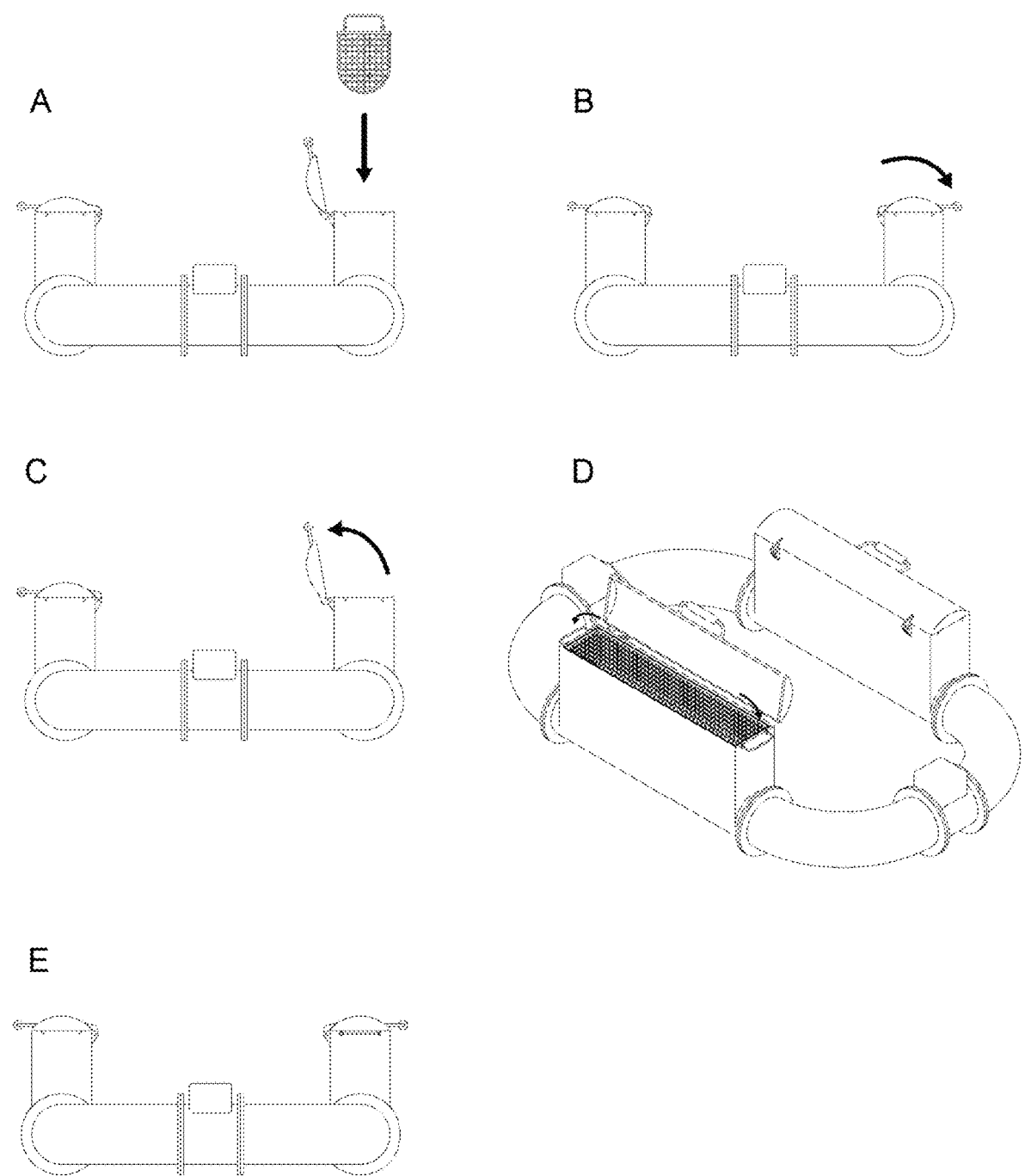
FIGS. 9A to 9E illustrate operation of a process.

The process of the invention can be further described by the schematic drawings in the FIGS. 7-9. FIG. 7 shows a closed loop 1 having a steeping reservoir 2, which that can be placed in a specially designed chamber 3 for holding the steeping reservoir 2. Closed loop 1 further comprises a heating element 4 and a pump and/or propeller 5 for moving the oil.

FIG. 8 shows that the closed loop may comprise multiple loops, which allows for increasing the capacity in plants (by having more steeping reservoirs), and allows for increasing the output capacity (by having more oil in the closed loop).

The operation of the process of the invention is schematically illustrated in FIGS. 9A-9E. In FIG. 9A the steeping reservoir is loaded with plant material and lowered into the flowing heated oil using a chamber which is specially designed to receive the steeping reservoir. Next, the lid of the chamber is closed (FIG. 9B). After some time, the lid of the chamber is opened (FIG. 9C) and the steeping reservoir is lifted above the oil surface (FIG. 9D). Suitably, the steeping reservoir can be locked into position above the oil surface. In FIG. 9E, the lid is closed again and the steeping reservoir is left above the oil surface for some time in order to drain the plant material. After a period of time, the lid is opened again and the steeping reservoir with plant material is replaced with a steeping reservoir containing new plant material.

The invention has been described by reference to various embodiments, and methods. The skilled person understands that features of various embodiments and methods can be combined with each other.

All references cited herein are hereby completely incorporated by reference to the same extent as if each reference were individually and specifically indicated to be incorporated by reference and were set forth in its entirety herein.

The use of the terms "a" and "an" and "the" and similar referents in the context of describing the invention (especially in the context of the claims) are to be construed to cover both the singular and the plural, unless otherwise indicated herein or clearly contradicted by context. The terms "comprising", "having", "including" and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. For the purpose of the description and of the appended claims, except where otherwise indicated, all numbers expressing amounts, quantities, percentages, and so forth, are to be understood as being modified in all instances by the term "about". Also, all ranges include any combination of the maximum and minimum points disclosed and include any intermediate ranges therein, which may or may not be specifically enumerated herein.

Preferred embodiments of this invention are described herein. Variation of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject-matter recited in the claims appended hereto as permitted by applicable law. Moreover, any combination of the above-described elements in all possible variations thereof is encompassed by the invention unless otherwise indicated herein or otherwise clearly contradicted by context. The claims are to be construed to include alternative embodiments to the extent permitted by the prior art.

For the purpose of clarity and a concise description features are described herein as part of the same or separate embodiments, however, it will be appreciated that the scope of the invention may include embodiments having combinations of all or some of the features described. Hereinafter, the invention will be illustrated in more detail, according to specific examples. However, the invention may be embodied in many different forms and should not be construed as being limited to the embodiments set forth herein. Rather, these example embodiments are provided so that this description will be thorough and complete, and will fully convey the scope of the invention to those skilled in the art.

EXAMPLES

Example 1—Extraction Process

The starting material was fresh hemp having a moisture content within 50-95% by total weight of the hemp. Part of the fresh hemp was dried in an oven at 60-80° C. until the hemp had a moisture content within 1-30%, based on the total weight of the hemp. Olive oil (Squisito Extra Vierge; obtained from a wholesaler) was heated to 60° C. The oil and hemp were brought into contact with each other while the oil and hemp were in motion relative to each other. During the extraction, hemp was replaced with new hemp. Oil fractions were collected (table 1).

TABLE 1

| Hemp | Concentration THCa (mg/ml) | Concentration THC (mg/ml) |
|---|---|---|
| Dried | 0.98 | ~0 |
| Fresh | 4.35 | <0.03 |

The invention claimed is:

1. A process for the extraction of one or more oil-soluble components from plant material comprising:
   a) providing oil and plant material;
   b) heating the oil to a temperature of 10-100° C.;
   c) contacting the oil with the plant material while the oil and plant material are in motion relative to each other, thereby extracting one or more oil-soluble components from said plant material;
   d) replacing plant material with new plant material during the extraction process, and
   e) collecting said oil when the concentration of the one or more oil-soluble components has reached a desired level;
   wherein said oil comprises vegetable oil; the plant material comprises trichomes; and the one or more oil-soluble components are selected from the group consisting of cannabinoids, flavonoids, and terpenes.

2. The process of claim 1, wherein the oil is present in a closable container, and wherein said oil is contacted with plant material contained in one or more steeping reservoirs, thereby extracting one or more oil-soluble components from said plant material.

3. The process of claim 1, wherein the oil of a) is continuously flowing in a closed loop, thereby establishing an oil flow, the oil is heated in said closed loop, and wherein said oil is contacted with plant material contained in one or more steeping reservoirs, thereby extracting one or more oil-soluble components from said plant material.

4. The process of claim 1, wherein the plant material is intact.

5. The process of claim 1, wherein the plant material has a moisture content of 1-95% by total weight of the plant material.

6. The process of claim 1, further comprising a step of monitoring the concentration of the one or more oil-soluble components in the oil during the extraction.

7. The process of claim 3, wherein said one or more steeping reservoirs are flow-through reservoirs.

8. The process of claim 1, wherein said one or more oil-soluble components comprise one or more selected from the group consisting of cannabinoids and terpenes.

9. The process of claim 1, further comprising a step of heating the oil wherein the one or more oil-soluble components are dissolved to a temperature in the range of for a period of 60-240 minutes.

10. The process of claim 9, wherein said further step of heating the oil is performed when said desired concentration level of the one or more oil-soluble components has been reached and before collecting the oil.

11. The process of claim 9, wherein the step of heating the oil decarboxylates at least part of the one or more oil-soluble components.

12. The process of claim 1, wherein the plant material is fresh plant material.

13. The process of claim 1, wherein said plant material comprises industrial hemp and/or marijuana.

14. The process of claim 1, wherein said plant material is contained in two or more steeping reservoirs.

15. The process of claim 1, further comprising contacting the plant material with an aqueous extractant.

16. The process of claim 3, wherein said replacing of plant material with new plant material is performed by removing one or more steeping reservoirs holding plant material from the oil flow and placing one or more steeping reservoirs holding new plant material into the oil flow.

17. The process of claim 1, wherein the process comprises multiple steeping reservoirs holding plant material which are alternately replaced.

18. The process of claim 3, wherein a direction of the oil flow in said closed loop is reversed one or more times during the process.

19. The process of claim 6, wherein said monitoring comprises the taking of samples and analysis thereof by High Performance Liquid Chromatography.

20. The process of claim 1, wherein one or more additives are added during the process, wherein said one or more additives comprise a natural emulsifier.

21. The process of claim 20, wherein said one or more additives comprise lecithin.

22. The process of claim 2, comprising additional agitation of the steeping reservoirs and the plant material contained therein.

23. The process of claim 3, wherein said closed loop is a horizontal loop.

24. An oil comprising vegetable oil and one or more oil-soluble components extracted from fresh plant material, wherein the oil contains at least 0.5% by weight of contaminants and less than 5% by weight of natural emulsifier, wherein the one or more oil-soluble components are one or more cannabinoids and one or more terpenes, and wherein the total of cannabinoids and the total of terpenes are in a weight ratio of 50:1 to 5:1.

25. A physiologically acceptable product comprising the oil of claim 24.

26. The physiologically acceptable product of claim 25 in a form suitable for oral application.

27. The process of claim 1, wherein said oil comprises one or more selected from the group consisting of olive oil, grapeseed oil, safflower oil, canola oil, sunflower oil, coconut oil, hemp seed oil, palm oil, palm kernel oil, soybean oil, peanut oil, almond oil, cottonseed oil, and rapeseed oil.

28. The oil of claim 24, wherein the one or more oil-soluble components are extracted from intact fresh plant material.

29. The oil comprising one or more oil-soluble components of claim 24, wherein the oil contains no natural emulsifier.

* * * * *